US010456749B2

(12) United States Patent
Handagama et al.

(10) Patent No.: US 10,456,749 B2
(45) Date of Patent: Oct. 29, 2019

(54) SYSTEM FOR THE REMOVAL OF HEAT STABLE AMINE SALTS FROM AN AMINE ABSORBENT

(71) Applicants: General Electric Technology GmbH, Baden (CH); DOW GLOBAL TECHNOLOGIES LLC, Midland, MI (US)

(72) Inventors: Nareshkumar B. Handagama, Sugar Land, TX (US); Barath Baburao, Knoxville, TN (US); Frederic Vitse, West Hartford, CT (US); Stephen A. Bedell, Knoxville, TN (US); Jonathan W. Leister, Manvel, TX (US); Ross Dugas, Pearland, TX (US)

(73) Assignees: General Electric Technology GMBH, Baden (CH); Dow Global Technologies LLC, Midland, MI (US)

( * ) Notice: Subject to any disclaimer, the term of this patent is extended or adjusted under 35 U.S.C. 154(b) by 57 days.

(21) Appl. No.: 15/253,243

(22) Filed: Aug. 31, 2016

(65) Prior Publication Data

US 2016/0367944 A1 Dec. 22, 2016

Related U.S. Application Data

(62) Division of application No. 13/248,344, filed on Sep. 29, 2011, now abandoned.

(60) Provisional application No. 61/454,079, filed on Mar. 18, 2011.

(51) Int. Cl.
*B01D 53/14* (2006.01)
*B01D 61/42* (2006.01)
(Continued)

(52) U.S. Cl.
CPC ....... *B01D 61/422* (2013.01); *B01D 53/1425* (2013.01); *B01D 53/1475* (2013.01); *B01D 53/1493* (2013.01); *B01D 61/42* (2013.01); *B01J 47/00* (2013.01); *C07C 209/84* (2013.01); *B01D 2252/204* (2013.01);
(Continued)

(58) Field of Classification Search
CPC .... B01D 2252/204; B01D 2252/20484; B01D 2252/20489; B01D 2257/504; B01D 2258/0283; B01D 2259/4009; B01D 53/1425; B01D 53/1475; B01D 53/1493; B01D 61/42; B01D 61/422; B01J 47/00;
(Continued)

(56) References Cited

U.S. PATENT DOCUMENTS 2,768,945 A   10/1956   Shapiro
3,554,690 A   1/1971    Maryland et al.
(Continued)

FOREIGN PATENT DOCUMENTS

CA    2824950 A1    8/2012
EP    0286143 A1    10/1988
(Continued)

OTHER PUBLICATIONS

Heat: Stable Salt Management, DOW, Jul. 2004, 4 pgs.

*Primary Examiner* — Cabrena Holecek
(74) *Attorney, Agent, or Firm* — McNees Wallace & Nurick LLC

(57) ABSTRACT

A system for the removal of heat stable amine salts from an amine absorbent used in a carbon dioxide ($CO_2$) capture process.

16 Claims, 2 Drawing Sheets

(51) Int. Cl.
  *B01J 47/00* (2017.01)
  *C07C 209/84* (2006.01)
(52) U.S. Cl.
  CPC .............. *B01D 2252/20484* (2013.01); *B01D 2252/20489* (2013.01); *B01D 2257/504* (2013.01); *B01D 2258/0283* (2013.01); *B01D 2259/4009* (2013.01); *Y02A 50/2342* (2018.01); *Y02C 10/04* (2013.01); *Y02C 10/06* (2013.01); *Y02C 10/08* (2013.01)
(58) Field of Classification Search
  CPC ... C07C 209/84; Y02A 50/2342; Y02C 10/04; Y02C 10/06; Y02C 10/08
  See application file for complete search history.

(56) References Cited

U.S. PATENT DOCUMENTS

| | | | |
|---|---|---|---|
| 4,245,569 A | 1/1981 | Fallon, III | |
| 5,292,407 A | 3/1994 | Roy et al. | |
| 5,338,521 A | 8/1994 | Quinn et al. | |
| 5,601,784 A | 2/1997 | Glover et al. | |
| 6,187,277 B1 | 2/2001 | Kirschner | |
| 2002/0020625 A1 | 2/2002 | Byszewski | |
| 2005/0000360 A1* | 1/2005 | Mak .................. | B01D 53/1475 95/236 |
| 2007/0148068 A1 | 6/2007 | Burgers et al. | |
| 2008/0159937 A1* | 7/2008 | Ouimet .............. | B01D 53/1475 423/230 |
| 2009/0317316 A1 | 12/2009 | McLauchlan et al. | |
| 2010/0074828 A1 | 3/2010 | Singh | |
| 2013/0309155 A1* | 11/2013 | Parisi ................ | B01D 53/1425 423/229 |

FOREIGN PATENT DOCUMENTS

| | | |
|---|---|---|
| EP | 0602675 A2 | 6/1994 |
| EP | 0810904 A1 | 12/1997 |
| EP | 1216744 A1 | 6/2002 |
| WO | 9626007 A1 | 8/1996 |
| WO | 2010142716 A1 | 12/2010 |
| WO | 2012100330 A1 | 8/2012 |

* cited by examiner

SYSTEM FOR THE REMOVAL OF HEAT STABLE AMINE SALTS FROM AN AMINE ABSORBENT

CROSS-REFERENCE TO RELATED APPLICATIONS

The present application is a divisional application of co-pending patent application Ser. No. 13/248,344, entitled "METHOD FOR THE REMOVAL OF HEAT STABLE AMINE SALTS FROM AN AMINE ABSORBENT" filed Sep. 29, 2011, which claims the benefit under 35 U.S.C. § 119(e) of Provisional Patent Application Ser. No. 61/454,079 entitled "METHOD FOR THE REMOVAL OF HEAT STABLE AMINE SALTS FROM AN AMINE ABSORBENT" filed Mar. 18, 2011, the disclosures of which are incorporated herein by reference in their entirety.

FIELD OF THE INVENTION

The proposed invention relates to a system and a method for the removal of heat stable amine salts from an amine absorbent used in a carbon dioxide ($CO_2$) capture process.

BACKGROUND

In the combustion of a fuel, such as coal, oil, natural gas, peat, waste, etc., in a combustion plant, such as those associated with boiler systems for providing steam to a power plant, a hot process gas (or flue gas) is generated. Such a flue gas will often contain, among other things, carbon dioxide ($CO_2$). The negative environmental effects of releasing carbon dioxide to the atmosphere have been widely recognized, and have resulted in the development of processes adapted for removing carbon dioxide from the hot process gas generated in the combustion of the above mentioned fuels.

In processes used for industrial separation of $CO_2$, liquid solutions comprising amine compounds are commonly used as an absorbent. Examples of amine compounds commonly used in absorption of $CO_2$ from gas streams include monoethanolamine (MEA), diethanolamine (DEA), methyldiethanolamine (MDEA), diisopropylamine (DIPA) and aminoethoxyethanol (diglycolamine) (DGA). The most commonly used amines compounds in industrial plants are the alkanolamines MEA, DEA, and MDEA.

$CO_2$ in the gas stream is captured in the liquid absorbent solution in an absorption process. A $CO_2$ absorber is employed to establish suitable conditions (temperature, pressure, turbulence, etc.) for chemical absorption of $CO_2$ into the amine absorbent from a mixed gas stream.

The amine absorbent containing absorbed $CO_2$ is subsequently regenerated, whereby absorbed $CO_2$ is separated from the absorbent, and the regenerated absorbent is then reused in the $CO_2$ absorption process. Thus, a circulating absorbent stream is formed. Regeneration is generally achieved by heating the amine absorbent in a stripper reboiler to a temperature at which $CO_2$ is released from the absorbent.

In the regenerator reboiler the absorbent is subjected to high temperature (generally about 115° C. or higher), whereas in the absorber the absorbent is exposed to higher $O_2$ environment. As a result of the exposure to high temperature and/or the presence of $O_2$, the amine solvent(s) of the absorbent may undergo degradation, whereby undesired degradation products are formed in the liquid phase. These degradation products, known as heat stable salts or heat stable amine salts (HSS), may accumulate in the circulating absorbent stream. The HSS reduce the $CO_2$ removal potency of the absorbent and may therefore preferably be removed from the absorbent stream. A common method of HSS removal is to take a slipstream from the circulating absorbent, separate the bulk absorbent from the HSS in a reclaimer and recycle the separated amine back to the circulating absorbent loop as reclaimed absorbent. A relaimer can consist of a distillation, ion exchange, or electrodialysis unit.

SUMMARY OF THE INVENTION

It is an object of the present invention to provide an improved system and process for removal of heat stable salts (HSS) from an amine absorbent stream used in a used in a carbon dioxide ($CO_2$) capture process.

In amine based $CO_2$ capture systems, a separation step, e.g. electrodialysis (ED), is often employed for separating amine absorbent from the undesired HSS in order to recycle the absorbent in the capture process. It has been found, however, that $CO_2$ in the amine absorbent can be detrimental to the separation process, such as electrodialysis.

Amine based $CO_2$ capture systems are sometimes operated in a way such that a relatively high $CO_2$ loading is observed in the lean solvent leaving the stripper. It has been found that when a slip stream of the lean solvent is sent to the reclamation unit, either electrodialysis or ion exchange, the relatively high lean loading fed to the reclamation unit results in significant quantities of amine lost through the reclamation waste stream. Reduced amine losses can significantly reduce amine make-up of the system and provide an economic advantage.

As a solution to this problem, there is provided a method and a system, wherein the amine absorbent containing the heat stable salts to be removed is first subjected to stripping and/or flashing, e.g. in a stripper or flash drum respectively, to remove residual $CO_2$, before being forwarded to the amine reclaimer for separation of amine absorbent from the HSS. The stripping/flashing step is simple and reliable, involves low additional investment and operational costs, and is easy to integrate into existing systems. Stripping is performed in a stripper, wherein the incoming amine absorbent is heated, e.g. by steam or electricity, to a temperature at which more volatile components, such as $CO_2$ in this case, are at least partly evaporated and leave the stripper via a gas/vapor exit. Stripping may be performed at atmospheric pressure or at increased or reduced pressure as necessary. Less volatile components, such as the bulk amine absorbent in this case, remain in liquid form and leave the stripper via a liquid exit. Flashing is generally performed in a flash drum, wherein the incoming amine absorbent undergoes a reduction in pressure, e.g. by passing through a throttling valve or other throttling device. More volatile components, such as $CO_2$, are at least partly evaporated and leave the flash drum via a gas/vapor exit. Less volatile components, such as the bulk amine absorbent in this case, remain in liquid form and leave the flash drum via a liquid exit. The stripping/flashing step should result in a reduction of the amount of $CO_2$ in the amine absorbent.

According to aspects illustrated herein, there is provided a method for the removal of heat stable amine salts from an amine absorbent used in a carbon dioxide ($CO_2$) capture process, comprising:

withdrawing amine absorbent containing heat stable amine salts from the $CO_2$ capture process;

subjecting the withdrawn amine absorbent containing heat stable amine salts to a residual $CO_2$ removal step;

subjecting the amine absorbent from the residual $CO_2$ removal step to a separation step to separate heat stable amine salts from the amine absorbent; and returning the amine absorbent having a reduced concentration of heat stable amine salts to the $CO_2$ capture process.

According to embodiments, the residual $CO_2$ removal step comprises stripping and/or flashing the withdrawn amine absorbent to remove residual $CO_2$.

According to embodiments, the residual $CO_2$ removal step comprises stripping the withdrawn amine absorbent to remove residual $CO_2$.

According to embodiments, the residual $CO_2$ removal step comprises flashing the withdrawn amine absorbent to remove residual $CO_2$.

According to embodiments, the residual $CO_2$ removal step comprises stripping and then flashing the withdrawn amine absorbent to remove residual $CO_2$.

According to embodiments, the flashing is performed under near vacuum conditions. By performing flashing at near vacuum conditions the absorbent may be kept at relatively low temperature. In addition to saving energy required for heating the absorbent, this also reduces the exposure of the absorbent to higher temperatures which could cause further degradation of the absorbent. The flashing may for example be performed at a pressure in the range of 0-2 bar gauge.

The method for the removal of heat stable amine salts from an amine absorbent is useful in a carbon dioxide ($CO_2$) capture process comprising regeneration of the amine absorbent at elevated temperatures. When performed in such a process, the method for the removal of heat stable amine salts can be operated with little additional energy requirement, by withdrawing the slipstream of amine absorbent from a point in the process where the amine absorbent has a low $CO_2$ loading.

Thus, according to embodiments, the $CO_2$ capture process comprises:

scrubbing a gas stream comprising $CO_2$ with an amine absorbent such that a $CO_2$ rich amine absorbent is formed;

regenerating the $CO_2$ rich amine absorbent by heating it to separate $CO_2$ from the amine absorbent, such that a $CO_2$ lean amine absorbent is formed; and recycling regenerated $CO_2$ lean amine absorbent to the scrubbing step.

It has been found that for the purposes of the present method for the removal of heat stable amine salts, the slipstream of amine absorbent containing HSS may advantageously be withdrawn from the lean amine absorbent from the regenerator. More particularly, the slipstream of amine absorbent may be withdrawn from the regenerator or from the liquid conduit between the regenerator and a lean absorbent/rich absorbent heat exchanger. The lean amine absorbent from the regenerator generally has a temperature of 100° C. or higher. This allows the thermal energy provided to the lean amine absorbent in the regenerator to be utilized in the stripping and/or flashing step. If necessary, the slipstream of lean amine absorbent containing HSS may also be withdrawn from the lean absorbent/rich absorbent heat exchanger or from the liquid conduit between the lean absorbent/rich absorbent heat exchanger and the $CO_2$ absorber performing the scrubbing step. When this is the case, the temperature of the slipstream of lean amine absorbent containing HSS may have a temperature of less than 100° C.

According to embodiments, the withdrawn amine absorbent containing heat stable amine salts is regenerated $CO_2$ lean amine absorbent.

According to embodiments, the regenerated $CO_2$ lean amine absorbent has a temperature of at least 100° C., such as at least 120° C.

According to embodiments, the separation step comprises subjecting the amine absorbent from the residual $CO_2$ removal step to electrodialysis and/or ion exchange.

According to embodiments, the separation step comprises subjecting the amine absorbent from the residual $CO_2$ removal step to electrodialysis.

According to embodiments, the separation step comprises subjecting the amine absorbent from the residual $CO_2$ removal step to ion exchange.

According to embodiments, the method further comprises cooling the amine absorbent from the residual $CO_2$ removal step before subjecting it to the separation step.

According to embodiments, the method further comprises subjecting the amine absorbent from the residual $CO_2$ removal step to indirect heat exchange with the amine absorbent coming from the separation step.

According to other aspects illustrated herein, there is provided a carbon dioxide ($CO_2$) capture system using an amine absorbent for absorption of $CO_2$ from a gas stream, having a subsystem for the removal of heat stable amine salts from an amine absorbent, said subsystem comprising:

a residual $CO_2$ removal unit in liquid connection with, and configured to receive, an amine absorbent stream containing heat stable amine salts from the $CO_2$ capture system, and operative for separating residual $CO_2$ from said amine absorbent stream; and an amine reclaimer in liquid connection with, and configured to receive, an amine absorbent stream containing heat stable amine salts and having a reduced concentration of $CO_2$ from the residual $CO_2$ removal unit, and operative for separating heat stable amine salts from said amine absorbent stream.

According to embodiments, the residual $CO_2$ removal unit comprises a stripper and/or a flash drum.

According to embodiments, the residual $CO_2$ removal unit comprises a stripper.

According to embodiments, the residual $CO_2$ removal unit comprises a flash drum.

According to embodiments, the residual $CO_2$ removal unit comprises a stripper and a flash drum arranged in series.

The stripper or flash drum provides for inexpensive, efficient and reliable removal of residual $CO_2$ from amine absorbent containing HSS before the absorbent is fed to the amine reclaimer for separation of heat stable amine salts.

The use of a stripper or flash drum for removal of residual $CO_2$ from an amine absorbent containing HSS is useful in a carbon dioxide ($CO_2$) capture system which regenerates the amine absorbent at elevated temperatures. When used in such a system, the stripper or flash drum can be operated with little additional energy requirement, by withdrawing the slipstream of amine absorbent from a point in the process where the amine absorbent has a low $CO_2$ loading.

According to embodiments, the carbon dioxide ($CO_2$) capture system comprises:

a $CO_2$ absorber operative for scrubbing a gas stream comprising $CO_2$ with an amine absorbent such that a $CO_2$ rich amine absorbent is formed;

a regenerator operative for regenerating $CO_2$ rich amine absorbent by heating it to separate $CO_2$ from the amine absorbent, such that a $CO_2$ lean amine absorbent is formed.

It has been found that for the purposes of the present method for the removal of heat stable amine salts, the slipstream of amine absorbent containing HSS may advantageously be withdrawn from the lean amine absorbent from the regenerator. More particularly, the slipstream of amine absorbent may be withdrawn from the regenerator or from the liquid conduit between the regenerator and a lean absorbent/rich absorbent heat exchanger. The lean amine absorbent from the regenerator generally has a temperature of 100° C. or higher, such as 120° C. or higher. This allows the thermal energy provided to the lean amine absorbent in the regenerator to be utilized in the stripping and/or flashing step. If necessary, the slipstream of lean amine absorbent containing HSS may also be withdrawn from the lean absorbent/rich absorbent heat exchanger or from the liquid conduit between the lean absorbent/rich absorbent heat exchanger and the $CO_2$ absorber performing the scrubbing step.

According to embodiments, the residual $CO_2$ removal unit is in liquid connection with, and configured to receive, an amine absorbent stream from the regenerator, and operative for separating residual $CO_2$ from the $CO_2$ lean amine absorbent.

According to embodiments, the amine reclaimer comprises an electrodialysis unit or an ion exchange unit.

According to embodiments, the amine reclaimer comprises an electrodialysis unit.

According to embodiments, the amine reclaimer comprises an ion exchange unit.

According to embodiments, the subsystem for removal of heat stable amine salts further comprises an amine absorbent cooler arranged between the residual $CO_2$ removal unit and the reclaimer and operative for cooling the amine absorbent from the residual $CO_2$ removal unit before it enters the reclaimer.

According to embodiments, the subsystem for removal of heat stable amine salts further comprises an indirect heat exchanger operative for subjecting the amine absorbent from the residual $CO_2$ removal unit to indirect heat exchange with the amine absorbent coming from the reclaimer.

The above described and other features are exemplified by the following figures and detailed description. Further objects and features of the present invention will be apparent from the description and the claims.

BRIEF DESCRIPTION OF THE DRAWINGS

Referring now to the figures, which are exemplary embodiments, and wherein the like elements are numbered alike.

DETAILED DESCRIPTION OF PREFERRED EMBODIMENTS

The term "amine absorbent" or simply "absorbent", as used herein, refers to a liquid composition comprising at least one amine compound useful in absorption of $CO_2$ from gas streams. Such compositions and suitable amine compounds are well known to a person skilled in the art. Examples of amine compounds commonly used in absorption of $CO_2$ from gas streams include, but are not limited to, monoethanolamine (MEA), diethanolamine (DEA), methyldiethanolamine (MDEA), diisopropylamine (DIPA) and aminoethoxyethanol (diglycolamine) (DGA). The most commonly used amines compounds in industrial plants are the alkanolamines MEA, DEA, and MDEA. The absorbent may comprise a single amine compound or a mixture of two or more amine compounds. In addition, the absorbent may comprise up to about 90% by volume of water, for example from about 50 to about 90% by volume of water. The absorbent may also comprise varying amounts of absorbed $CO_2$. Absorbent containing none or only a low concentration of absorbed $CO_2$, e.g. following regeneration, is referred to as "$CO_2$ lean" or simply "lean" absorbent, whereas absorbent containing higher concentrations of absorbed $CO_2$, e.g. following absorption, is referred to as "$CO_2$ rich" or simply "rich" absorbent.

Figure 1:
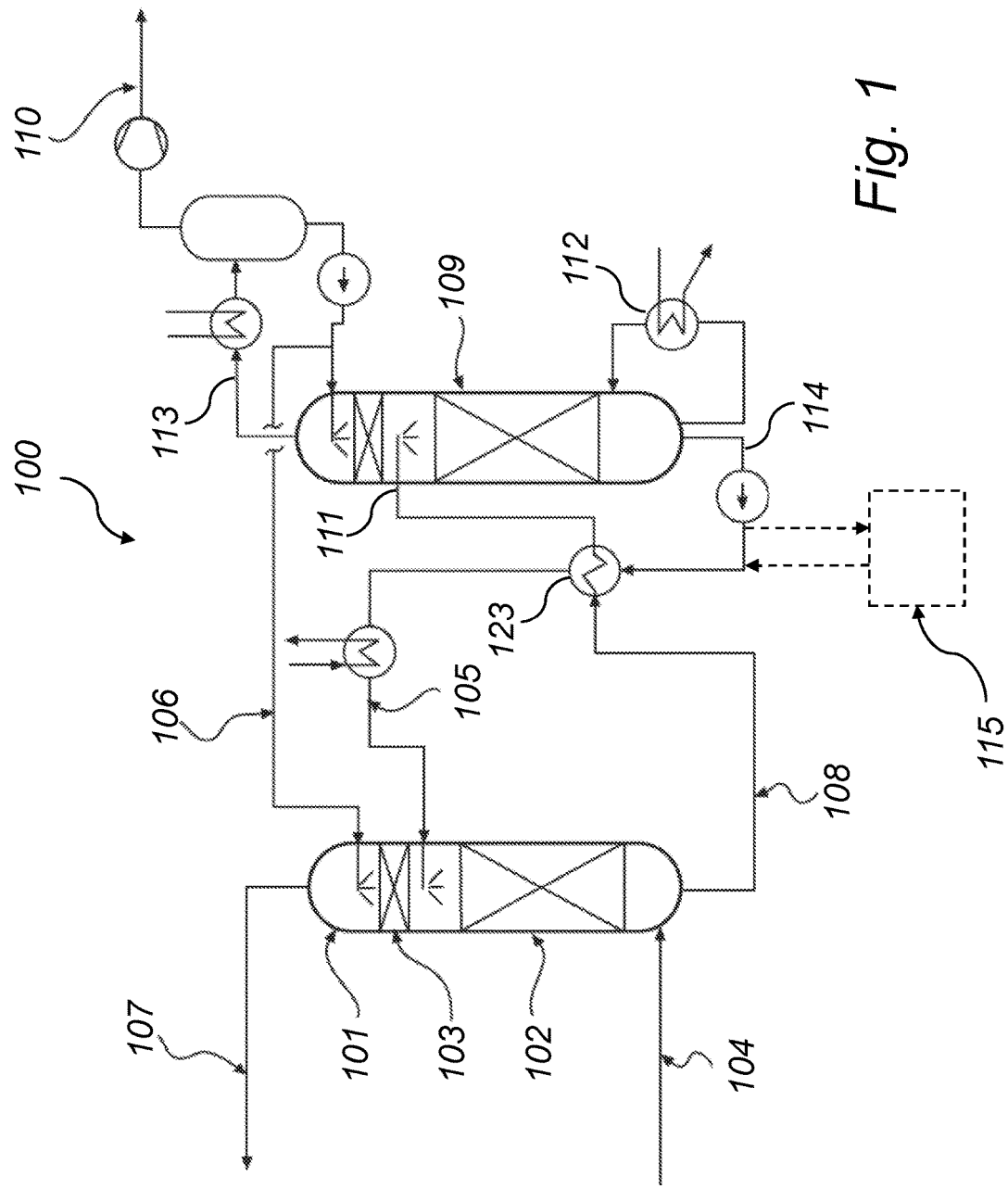
FIG. 1 is a diagram generally depicting an amine based gas purification system comprising an amine absorbent reclaimer circuit.

FIG. 1 is a schematic representation of an amine based carbon dioxide ($CO_2$) capture system (100). The system comprises an absorption unit (101) arranged to allow contact between a gas stream to be purified and one or more wash liquids. The absorption unit represented in FIG. 1 comprises a $CO_2$ absorption section (102) and a water wash section (103). Flue gas, from which $CO_2$ is to be removed, is fed to the absorption unit (101) via line (104). In the $CO_2$ absorption section (102), the flue gas is contacted with a first wash liquid comprising an amine compound, e.g. by bubbling the flue gas through said first wash liquid or by spraying the first wash liquid into the flue gas. The first wash liquid is fed to the absorption unit (101) via line (105). In the $CO_2$ absorption section (102) $CO_2$ from the flue gas is absorbed in the first wash liquid. Flue gas depleted of $CO_2$ in the $CO_2$ absorption section then enters the water wash section (103) of the absorption unit. The water wash section (103) is arranged to allow contact between the flue gas depleted of $CO_2$ from the $CO_2$ absorption section (102) and a second wash liquid, which is generally water. The second wash liquid is fed to the absorption unit via line (106). In the water wash section, contaminants remaining in the flue gas when it leaves the $CO_2$ absorption section are absorbed in the second wash liquid. Flue gas depleted of $CO_2$ and contaminants leaves the absorption unit via line (107). The used first and second wash liquid containing absorbed $CO_2$ and contaminants leave the absorption unit via line (108). The used first and second wash liquid may be recycled via a regenerator unit (109), wherein contaminants and $CO_2$ are separated from the wash water. The separated $CO_2$ leaves the system via line (110).

The used first and second wash liquid to be regenerated enters the regenerator (109) via line (111). In the regenerator, the used wash liquids are heated, generally using steam, in a reboiler (112). The heating causes desorption of absorbed $CO_2$ from the wash liquids. The desorbed $CO_2$ then exits the regenerator via line (113) together with some water vapor also formed during heating. Regenerated wash liquid, containing a reduced concentration of $CO_2$, leaves the regenerator (109) via line (114). The regenerated wash liquid is also referred to herein as "$CO_2$ lean amine absorbent" or simply "lean amine absorbent". The lean amine absorbent may also contain heat stable salts (HSS) formed as degradation products in the regenerator as a result of the exposure to high temperature and/or the presence of $O_2$ (absorbed by the absorbent in the absorption unit). The lean amine absorbent leaving the regenerator may be directed to a lean absorbent/rich absorbent heat exchanger (123) where it is used for pre-heating rich amine absorbent from line (108) directed towards the regenerator (109).

The amine based carbon dioxide ($CO_2$) capture system (100) may further comprise an amine absorbent reclaimer circuit (115) operative for at least partial removal of HSS from the circulating amine absorbent, so as to prevent accumulation of HSS and the problems associated therewith. The amine absorbent reclaimer circuit (115) is generally configured to withdraw a slipstream of the main amine absorbent flow. The amine absorbent reclaimer circuit (115) may preferably be configured to withdraw the slipstream of lean amine absorbent from a point in the process where the amine absorbent has a low $CO_2$ loading, i.e. lean amine absorbent. More particularly, the slipstream of amine absorbent may be withdrawn from the regenerator (109) or from the liquid conduit (114) between the regenerator (109) and a lean absorbent/rich absorbent heat exchanger (123). The lean amine absorbent from the regenerator generally has a temperature of 100° C. or higher, such as 120° C. or higher. This allows the thermal energy provided to the lean amine absorbent in the regenerator to be utilized in the stripping and/or flashing step. If necessary, the slipstream of lean amine absorbent containing HSS may also be withdrawn from the lean absorbent/rich absorbent heat exchanger (123) or from the liquid conduit (105) between the lean absorbent/rich absorbent heat exchanger (123) and the $CO_2$ absorber (101) performing the scrubbing step. The slipstream may generally comprise in the range of 0.001-50% by volume of the main amine absorbent flow, such as in the range of 0.01-10% by volume of the main amine absorbent flow.

Figure 2:
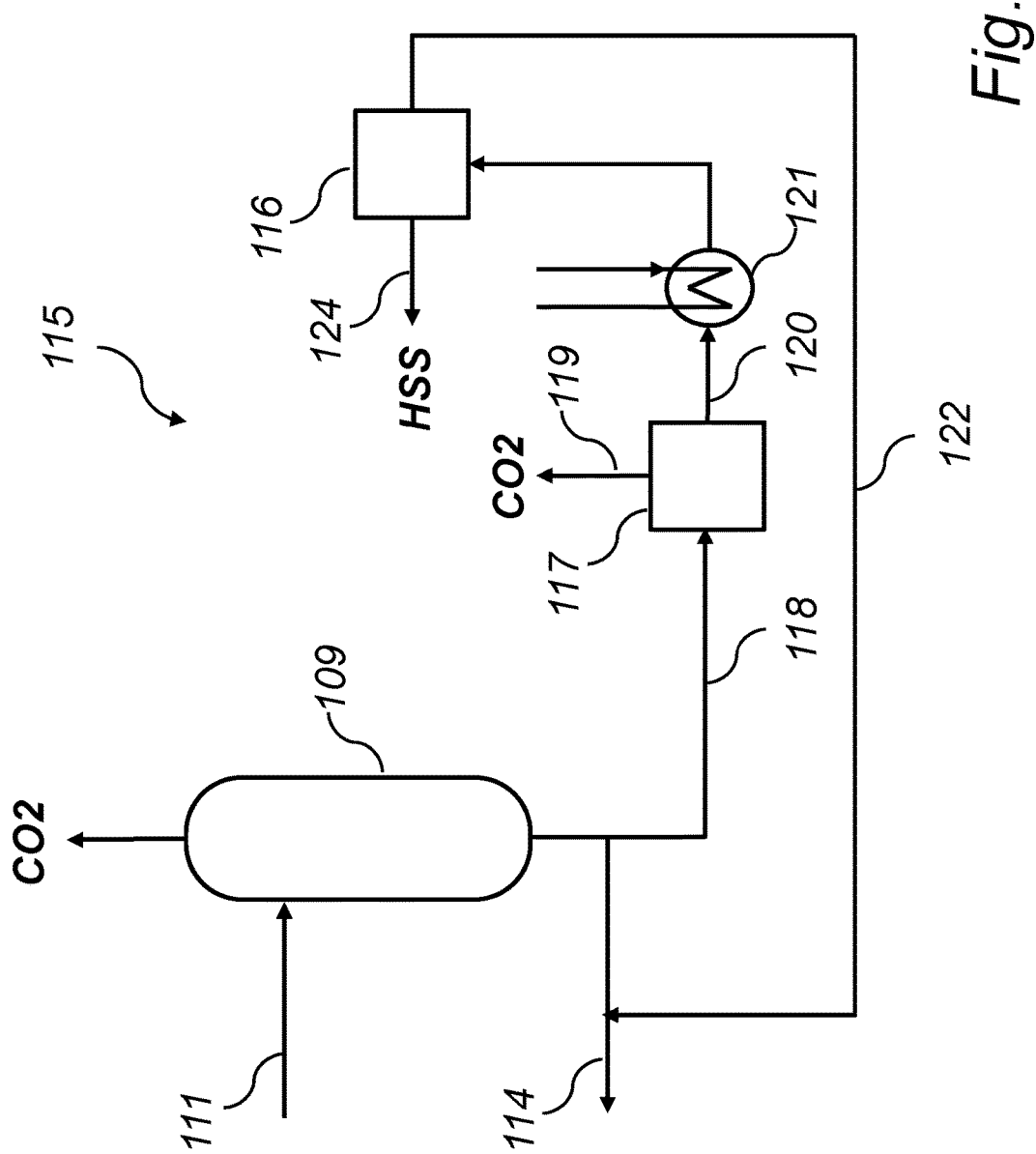
FIG. 2 is a diagram generally depicting an embodiment of an amine based gas purification system comprising an amine absorbent reclaimer circuit.

FIG. 2 represents an amine based carbon dioxide ($CO_2$) capture system according to the invention, comprising an amine absorbent reclaimer circuit (115). The amine absorbent reclaimer circuit (115) is connected to the regenerator side of an amine based carbon dioxide ($CO_2$) capture system, e.g. as described above with reference to FIG. 1.

The amine absorbent reclaimer circuit (115) comprises an amine reclaimer (116) for separating heat stable salts from the amine absorbent. In this embodiment, the amine reclaimer (116) is an electrodialysis (ED) unit.

The ED unit is used to transport salt ions, e.g. HSS, from the amine absorbent through ion-exchange membranes to another solution under the influence of an applied electric potential difference. This is done in a configuration called an electrodialysis cell. The cell consists of a feed (diluate) compartment and a concentrate (e.g. brine) compartment formed by an anion exchange membrane and a cation exchange membrane placed between two electrodes. Multiple electrodialysis cells may be arranged into a configuration called an electrodialysis stack, with alternating anion and cation exchange membranes forming the multiple electrodialysis cells. The ED process results in a reduction of HSS in the amine absorbent as HSS ions are concentrated in the concentrate solution.

In an alternative embodiment, the amine reclaimer (116) is an ion exchange unit comprising an ion exchange resin suitable for the removal of HSS ions from the amine absorbent.

The amine absorbent reclaimer circuit (115) further comprises a residual $CO_2$ removal unit (117) arranged upstream of the amine reclaimer (116) with reference to the lean amine absorbent stream. In the embodiment of FIG. 2 the residual $CO_2$ removal unit (117) is a flash drum. Flash (or partial) evaporation is the partial vaporization that occurs when a saturated liquid stream undergoes a reduction in pressure by passing through a throttling valve or other throttling device. If the throttling valve or device is located at the entry into a pressure vessel so that the flash evaporation occurs within the vessel, then the vessel is often referred to as a flash drum.

The flash drum (117) comprises a pressure vessel having a feed inlet, a gas outlet and a liquid outlet. The feed inlet is equipped with a throttling device configured to decrease the pressure of the feed stream before it enters the pressure vessel. The exact configuration of flash drums suitable for use in the system described herein will be readily recognized by a person skilled in the art.

The lean amine absorbent enters the flash drum (117) via a feed line (118). The temperature and pressure of the lean amine absorbent is determined by the temperature and pressure of the lean amine absorbent in, or leaving, the regeneration unit (109). The pressure of the lean amine absorbent may optionally be decreased by means of a throttling valve or device arranged in the feed inlet of the flash drum. In the flash drum (117), the pressure is then reduced, such that more volatile components, e.g. residual $CO_2$, at least partially evaporate, while less volatile components, e.g. amine absorbent and water, remain in liquid phase. The pressure inside of the flash drum may preferably be low, such as in the range of 0-2 bar gauge. Evaporated components, e.g. residual $CO_2$, leave the flash drum (117) through a gas outlet via line (119), while liquid components, e.g. amine absorbent and water, leave the flash drum (117) through a liquid outlet via line (120).

In an alternative embodiment, the residual $CO_2$ removal unit (117) is a stripper. The stripper may, for example, comprise a generally cylindrical steel vessel configured to operate within a pre-determined pressure range. The stripper is preferably equipped with one or more suitable mass transfer devices, such as valve trays, sieve trays, structured packing, random packing or other suitable packing materials, or a combination thereof. A heating system/device may be provided in the stripper for heating the amine absorbent. The stripper is preferably configured to provide sufficient heat to the amine absorbent so that low boiling point components, for example $CO_2$, are transferred to a gas phase, while high boiling point components, for example water and amine, are collected in a liquid phase at the bottom of the stripper. The amine absorbent may be heated up appropriately via, for example, a reboiler. The reboiler may be heated using, for example, electrically generated heat or steam. The stripper is configured to discharge the gas phase, containing $CO_2$, via a gas exit, and the liquid phase, containing water and amine, via a liquid exit.

In yet another alternative embodiment, the residual $CO_2$ removal unit (117) comprises a stripper and a flash drum arranged in series, such that a first portion of residual $CO_2$ may be removed in the stripper, and a second portion of residual $CO_2$ may be removed in the flash drum. The stripper and flash drum may be as described above. The lean amine absorbent first enters the stripper, where it is heated to a temperature sufficient to transfer low boiling point components, for example $CO_2$, to a gas phase, while high boiling point components, for example water and amine, are collected in a liquid phase at the bottom of the stripper. The liquid phase is then forwarded to the flash drum, where the pressure is reduced so that more volatile components, e.g. residual $CO_2$, at least partially evaporate, while less volatile components, e.g. amine absorbent and water, remain in liquid phase. The liquid components, e.g. amine absorbent and water, leave the flash drum through a liquid outlet and is forwarded to the reclaimer.

Referring now to FIG. 2, the lean amine absorbent, from which residual $CO_2$ has been at least partially removed, is forwarded via line (120) to the amine reclaimer (116), wherein heat stable salts are at least partially separated from the amine absorbent to produce a lean amine absorbent depleted in HSS.

Optionally, the amine absorbent reclaimer circuit (115) further comprises a cooler (121) arranged between the residual $CO_2$ removal unit (117) and amine reclaimer, and configured to adjust the temperature of the lean amine absorbent from the residual $CO_2$ removal unit before it enters the amine reclaimer (116).

Furthermore, an amine absorbent reclaimer circuit (115) comprising a cooler (121), may optionally further comprise an indirect heat exchanger (not shown) arranged between the residual $CO_2$ removal unit (117) and the cooler (121) and configured to cool the lean amine absorbent from the residual $CO_2$ removal unit (117) using the lean amine absorbent depleted in HSS leaving the amine reclaimer (116). The indirect heat exchanger may for example be a conventional plate or shell and tube type heat exchanger.

The lean amine absorbent depleted in HSS leaves the amine reclaimer (116) and is forwarded via return line (122) back to the $CO_2$ capture system (100). The lean amine absorbent depleted in HSS may, for example be reintroduced into the regenerator (109), absorber (101), or into a suitable liquid conduit connecting the regenerator (109) and absorber (101). The position for reintroduction of the lean amine absorbent from the amine reclaimer circuit may be selected depending on the specific temperature and pressure of the absorbent. One suitable position for reintroduction, as shown in FIG. 2, would be into line (114), either upstream or downstream of a lean absorbent/rich absorbent heat exchanger (123). The separated heat stable salts leave the amine reclaimer via line (124).

While the invention has been described with reference to a number of preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

Example—Amine Loss into the Waste Brine Stream of the Electrodialysis Unit

Amine losses from a lean amine absorbent into the waste brine of a 3-loop ElectroSep electrodialysis unit (ElectroSep Inc., USA) was evaluated with various $CO_2$ loadings in the lean amine absorbent. 1.2 and 1.4 wt % amine was observed in the waste brine stream when the lean amine absorbent had $CO_2$ loadings of 2.2 and 2.9 wt % $CO_2$, respectively. Only 0.3 wt % amine was observed in the waste brine stream with 0.01 wt % $CO_2$ in the lean amine absorbent. This represents a 75-80% reduction in amine losses compared to the higher lean loadings. This example shows that a significant reduction of amine losses can be achieved by reduction of the $CO_2$ loading of the lean amine absorbent, e.g. by stripping or flashing, prior to feeding it to a reclaimer unit, such as an electrodialysis unit.

The invention claimed is:

1. A carbon dioxide ($CO_2$) capture system using an amine absorbent for absorption of $CO_2$ from a gas stream, the $CO_2$ capture system comprising a subsystem for removal of heat stable amine salts from a slipstream comprising the amine absorbent, the subsystem comprising:
   a residual $CO_2$ removal unit in liquid connection with, and configured to receive, the slipstream containing heat stable amine salts from a $CO_2$-lean amine absorbent stream of the $CO_2$ capture system, and operative for separating residual $CO_2$ from the $CO_2$-lean amine absorbent stream; and
   an amine reclaimer in liquid connection with, and configured to receive, the slipstream containing heat stable amine salts and having a reduced concentration of $CO_2$ from the residual $CO_2$ removal unit, operative for separating heat stable amine salts from the slipstream, and configured to return the slipstream separated from heat stable amine salts to the $CO_2$-lean amine absorbent stream.

2. The $CO_2$ capture system according to claim 1, wherein the amine reclaimer comprises an electrodialysis unit or an ion exchange unit.

3. The $CO_2$ capture system according to claim 1, wherein the subsystem further comprises an amine absorbent cooler operationally arranged between the residual $CO_2$ removal unit and the reclaimer and operative for cooling the slipstream from the residual $CO_2$ removal unit before the slipstream enters the reclaimer.

4. The $CO_2$ capture system according to claim 1, wherein the subsystem further comprises an indirect heat exchanger operative for subjecting the slipstream from the residual $CO_2$ removal unit to indirect heat exchange with the slipstream coming from the reclaimer.

5. The $CO_2$ capture system according to claim 1, wherein the residual $CO_2$ removal unit comprises a stripper and/or a flash drum.

6. The $CO_2$ capture system according to claim 5, wherein the residual $CO_2$ removal unit comprises the stripper.

7. The $CO_2$ capture system according to claim 5, wherein the residual $CO_2$ removal unit comprises the flash drum.

8. The $CO_2$ capture system according to claim 5, wherein the residual $CO_2$ removal unit comprises the stripper and the flash drum arranged in series.

9. The $CO_2$ capture system according to claim 1 further comprising:
   a $CO_2$ absorber operative for scrubbing the gas stream comprising $CO_2$ with the amine absorbent such that a $CO_2$-rich amine absorbent stream is formed; and
   a regenerator operative for regenerating the $CO_2$-rich amine absorbent stream by heating the $CO_2$-rich amine absorbent stream to separate $CO_2$ from the amine absorbent, thereby forming the $CO_2$-lean amine absorbent stream.

10. The $CO_2$ capture system according to claim 9, wherein the slipstream is taken from the $CO_2$-lean amine absorbent stream from the regenerator.

11. The $CO_2$ capture system according to claim 9 further comprising an amine absorbent heat exchanger between the $CO_2$ absorber and the regenerator.

12. The $CO_2$ capture system according to claim 11, wherein the slipstream is taken from the $CO_2$-lean amine absorbent stream from the amine absorbent heat exchanger.

13. The $CO_2$ capture system according to claim 11, wherein the slipstream is taken from between the regenerator and the amine absorbent heat exchanger.

14. The $CO_2$ capture system according to claim 11, wherein the slipstream is taken from between the amine absorbent heat exchanger and the $CO_2$ absorber.

15. The $CO_2$ capture system according to claim 11, wherein the amine reclaimer comprises an electrodialysis unit.

16. The $CO_2$ capture system according to claim 11, wherein the amine reclaimer comprises an ion exchange unit.

* * * * *